US00PP09087P

United States Patent [19]

Mantel

[11] Patent Number: Plant 9,087

[45] Date of Patent: Mar. 21, 1995

[54] LILIUM 'TYROLIA'

[76] Inventor: Homme Mantel, P.O. Box 1314, Sandy, Oreg. 97055

[21] Appl. No.: 282,303

[22] Filed: Jul. 29, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

[57] ABSTRACT

A new variety of hybrid lily plant bearing upfacing flowers of excellent form and long persistence, both on the plant and as cut-flowers. The cream white flowers of the new hybrid are particularly characterized by their short, pollen-free, antherless filaments and their starry form, with all tepals approximately the same width. This combination is completely new in the Asiatic hybrid divisions of lilies suited to forcing and to mass commercial cultivation. The variety is resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 1989 in 't Zandt, the Netherlands. The breeding efforts had as their objective the production of Asiatic hybrid lilies with upfacing, pollen-free flowers, suited to forcing into flower out of season, heretofore unknown in the lily breeding art.

I achieved the desired objective by intercrossing a small-flowered, pollen-free white upfacing unnamed seedling with a tall, exceptionally vigorous, large-flowered orange unnamed seedling. Both parents were produced by me and never released. The seed parent for 'Tyrolia' was a pollen-free, albino-flowered mutant Asiatic hybrid produced by open-pollination of 'Sunkissed' (unpatented). 'Sunkissed' was commercially available as a garden lily during the 1970's. The pollen parent for 'Tyrolia' was produced by open pollination of 'Chinook' (unpatented). 'Chinook' was grown commercially in the United States and the Netherlands as a garden lily and cut-flower variety during the 1970's and 1980's.

The flowers of my new lily are characterized by upfacing cream white flowers with short, antherless, pollen-free filaments. The flowers have an unusual starry form, with all tepals approximately the same width. In addition, the clone possesses to a high degree desirable characteristics of hybrid vigor. The clone is a good grower and propagator, as observed at 't Zandt, the Netherlands.

My new variety of lily plant has been asexually reproduced by me and under my direction at 't Zandt, the Netherlands. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the starry flower form with all tepals approximately the same width, the tepal arrangement, and in particular the novel and distinctive short, antherless, pollen-free filaments.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Colour Chart of The Royal Horticultural Society, published by the Society in 1966.

The Plant

Origin: Seedling.

*Seed parent.*—Unnamed white pollen-free seedling.

*Pollen parent.*—Unnamed tall orange seedling.

Commercial classification: Hybrid Lilium clone.

Horticultural classification: Division I-A, Upfacing Asiatic Hybrid Lily, according to the Horticultural Classification of Lilies, Royal Horticultural Society of London.

Form: Single stem, erect and stately.

Height: 1.25 to 1.75 m from bulbs 12 to 16 cm in circumference, provided their light levels are adequate, low light levels may cause "stretching."

Growth: Vigorous and upright.

Foliage quantity: Abundant.

Size of leaf: 7 to 12 cm long, 2 to 4 cm wide.

Shape of leaf: Lanceolate (pointed).

Texture: Leathery and glossy.

Color: Very dark green, lighter on lower side.

Bulb:

*Size.*—Any size, ranging to 25 cm circumference commercially.

*Color.*—White, with flushes of pink or yellow after exposure to light.

The Bud

Form: Obtuse, ovoid, and long.

Size: 7 to 10 cm long and 7 to 12 cm in circumference just prior to opening.

Opening: Bud opens slowly, in response to morning light; this takes about one hour.

Color: Cream to white with green midribs and green tips just prior to opening.

Peduncle. Averages 5 to 8 cm, but it may elongate if light levels are too low, if bulbs have been improperly stored prior to forcing, or if bulbs are very large, producing an unusually large inflorescence. Color is deep plum over green, appearing almost black to the eye.

The Flower

Blooming habit; Annually in midseason, flowers once and profusely.

Size: Flowers are large, averaging 12 to 16 cm in diameter, flattening slightly at the tips on the second day to 12 to 15 cm in diameter. All tepals are approximately 2.5 to 3 cm wide.

Borne: In a single racemic inflorescence producing 8 to 12 flowers from a bulb 12 to 16 cm in circumference.

Shape: Starry, with all tepals approximately the same width and recurving only very slightly at the tips.

Tepalage: Typical of genus Lilium, with 6 imbricated tepals.

Tepal:

*Color.*—In cool weather, tepal base may show a flush of cream yellow RHS CC Yellow 4 C-D just above the nectaries, shading into pure white at the tips. Flowers will be pure white when temperatures are warm.

*Spotting.*—Flowers are virtually spotless, but occasionally they will show 2 to 4 inconspicuous deep magenta spots at the base of the inner tepals.

*Longevity.*—Tepals stay on stems about three weeks.

Nectaries: Nectaries are generally soft green, shading to ivory white when light is intense and temperatures warm. Nectaries are inconspicuous and lightly pubescent, with short white hairs noticeable only when the flower is completely open.

Pedicel:

*Length.*—Average 7 to 10 cm long.

*Color.*—Dark green with deep plum overlay; appear almost black to the eye.

*Form.*—Sturdy and ascending.

Color changes: Flowers become pure white and less cream-white as the flowers age. With very cool temperatures, tepal bases may remain cream-white.

Appearance: Flower is shiny.

Disease resistance: The flower and plant are resistant to disease; in particular, they are resistant to Fusarium bulb rot and Botrytis blight.

Fragrance: None.

Lasting quality: The flower is long lasting, both on the plant and as a cut-flower.

The Reproductive Organs

Stamens: Arrangement typical of genus Lilium. Six cream-white filaments 2–3 cm long which generally do not bear anthers.

Anthers: Generally absent; occasionally a tiny, pollen-free anther (1–4 mm in length) is produced, which does not dehisce.

Pistil: One in number, cream white to very soft apricot (RHS CC orange 27 D or lighter), 4 to 9 cm long.

Stigma: Soft plum (RHS CC greyed purple 185 C/D) in color, large in size.

Characteristics of ovary: Characteristics of genus Lilium.

The Fruit

Fertility: The fruit bears a fertile seed.

Shaped: Ovoid.

Color at maturity: Soft brown, overlaid with soft plum.

My new variety of Asiatic hybrid lily most nearly resembles its sibling 'Grandview' (U.S. Plant Pat. No. 8,763) in form of flower and inflorescence, but it has cream-white flowers with shorter filaments which generally bear no anthers.

I claim:

1. A new and distinctive variety of Asiatic hybrid lily plant substantially as herein shown and described, characterized by its high resistance to disease; its tolerance of virus; its vigorous growth and rapid natural propagation; the excellence of its flower form, size, and substance; its versatility both as a garden plant and as a cut-flower produced from pre-cooled bulbs forced under glass out of season; and in particular by its unique upfacing, cream-white pollen-free, antherless starry flowers with tepals all approximately the same width, a combination unique among hybrid lilies suited to forcing and to mass commercial cultivation.

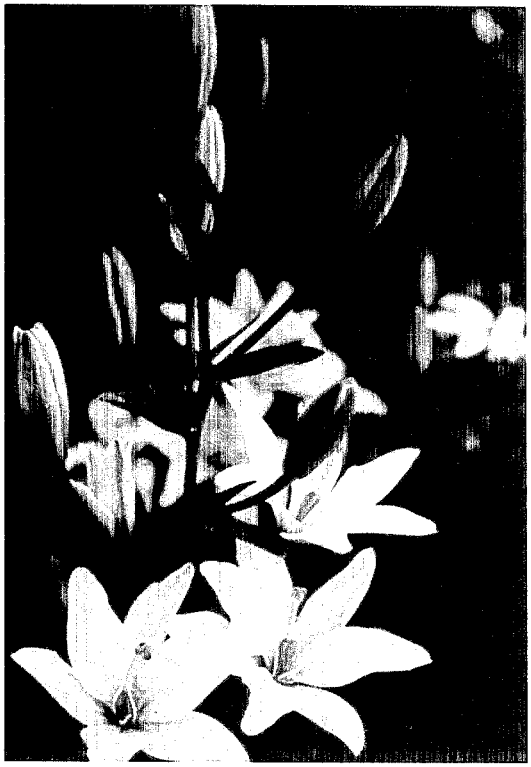

* * * * *